(12) United States Patent
Okuno

(10) Patent No.: US 8,950,937 B2
(45) Date of Patent: Feb. 10, 2015

(54) X-RAY INSPECTION APPARATUS

(75) Inventor: Tomoharu Okuno, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 122 days.

(21) Appl. No.: 13/885,661

(22) PCT Filed: Nov. 26, 2010

(86) PCT No.: PCT/JP2010/071092
§ 371 (c)(1),
(2), (4) Date: May 15, 2013

(87) PCT Pub. No.: WO2012/070143
PCT Pub. Date: May 31, 2012

(65) Prior Publication Data
US 2013/0235983 A1  Sep. 12, 2013

(51) Int. Cl.
*H05G 1/02* (2006.01)
*H05G 1/58* (2006.01)
*A61B 6/06* (2006.01)
*A61B 6/00* (2006.01)

(52) U.S. Cl.
CPC .. *H05G 1/02* (2013.01); *A61B 6/06* (2013.01); *A61B 6/4464* (2013.01)
USPC ............ 378/205; 378/114; 378/115; 378/116

(58) Field of Classification Search
USPC ............ 378/91, 95, 114–116, 189, 196–198, 378/204, 205, 210; 250/491.1
See application file for complete search history.

(56) References Cited

U.S. PATENT DOCUMENTS

2009/0257561 A1  10/2009  Okuno et al.
2010/0123083 A1   5/2010  Petrick et al.

FOREIGN PATENT DOCUMENTS

| JP | 2005-198881 A | 7/2005 |
| JP | 2007-020869 A | 2/2007 |
| JP | 2008-125981 A | 6/2008 |
| JP | 2010-119848 A | 6/2010 |
| JP | 2010-187862 A | 9/2010 |

OTHER PUBLICATIONS

International Search Report issued in International Application No. PCT/JP2010/071092 mailed. Jan. 18, 2011.

*Primary Examiner* — Anastasia Midkiff
(74) *Attorney, Agent, or Firm* — McDermott Will & Emery LLP

(57) ABSTRACT

When a size of a flat panel detector, contained in an X-ray detector containing part, in a body axial direction of a subject is detected, a detected value of a potentiometer, and stored information on a maximum size of a flat panel detector, containable in the X-ray detector containing part, in the body axial direction of the subject are compared with each other. If the size of the flat panel detector contained in the X-ray detector containing part coincides with the maximum size of the flat panel detector containable in the X-ray detector containing part, a reference position information switching part switches reference position information stored in a reference position information storage part. When an operator performs a predetermined operation on an operation part by pressing a switch or performing another action, the stored reference position information is changed to a preset reference position.

12 Claims, 10 Drawing Sheets

X-RAY INSPECTION APPARATUS

RELATED APPLICATIONS

This application is the U.S. National Phase under 35 U.S.C. §371 of International Application No. PCT/JP2010/071092, filed on Nov. 26, 2010, the disclosures of which Application is incorporated by reference herein.

TECHNICAL FIELD

The present invention relates to an X-ray inspection apparatus that photographs an X-ray image of a subject with X-rays irradiated from an X-ray tube.

BACKGROUND ART

In such an X-ray inspection apparatus, an X-ray detector such as a cassette, CR (Computed Radiography), or FPD (Flat Panel Detector) is used. In the X-ray inspection apparatus that photographs a subject in an upright position state, such as an upright position stand type, depending on a physical constitute of the subject or a subject's site to be photographed, a vertical position of the X-ray detector is changed and along with this, a vertical position of an X-ray tube is also changed.

The X-ray detector is contained in an X-ray detector containing part such as a bucky part. The X-ray detector containing part is configured to be able to contain any of X-ray detectors having various sizes other than an X-ray detector having a size corresponding to the X-ray detector containing part. When the X-ray detector is attached to the X-ray detector containing part, a reference position thereof is determined by upper reference based on an upper end of the X-ray detector containing part, center reference based on the center of the X-ray detector containing part, or lower reference based on a lower end of the X-ray detector containing part, and thereby the X-ray detector is configured to be mechanically fixed with use of a spring or the like. Any of such reference positions is conventionally determined in an unambiguous manner in association with mechanical structure of each X-ray detector containing part (see Patent Literature 1).

Also, for such an X-ray inspection apparatus, there is proposed a photography system that uses an anatomical program having data structure that relates a photographing condition, a subject' site to be photographed, a photographing method, and the like to one another, and according to the anatomical program and the like, automatically moves the X-ray tube to a photographing position (see Patent Literature 2). Further, the photographing position of the X-ray tube is calculated on the basis of a size of the X-ray detector and the reference position of the X-ray detector, such as the upper reference, center reference, or lower reference (see Patent Literature 3).

CITATION LIST

Patent Literature

Patent Literature 1: JP-A2005-198881
Patent Literature 2: JP-A2008-125981
Patent Literature 3: JP-A2007-20869

SUMMARY OF INVENTION

Technical Problem

In such an X-ray inspection apparatus, as described above, the reference position of the X-ray detector is unambiguously determined in association with the mechanical structure of the X-ray detector containing part. Also, on the basis of the reference position, the photographing position of the X-ray tube is also determined. For this reason, in the conventional X-ray inspection apparatus, it is impossible to use the X-ray detector with switching the reference position of the X-ray detector among the upper reference, the center reference, the lower reference, and the like.

Now, for example, assumed is the case where in an X-ray inspection apparatus that photographs a subject in an upright position state, such as an upright position stand type, a center reference-based X-ray detector containing part is used. In such a case, in the case of performing photography of a knee in the upright position, the center reference-based X-ray detector containing part is moved downward. Along with this, an X-ray tube is moved to a position facing to an X-ray detector in the X-ray detector containing part; however, the X-ray detector containing part is based on the center reference, and therefore the X-ray tube is also only moved to the position facing to the central part of the X-ray detector containing part. For this reason, if a position of the knee is a position lower than the position facing to the central part, and it is necessary to move down the X-ray tube to the lower position at any cost, it is necessary for an operator to move the X-ray tube through a manual operation or the like, which causes poor operability.

The present invention is made in order to solve the above problems, and intended to provide an X-ray inspection apparatus that changes a reference position so as to correspond to X-ray inspection, and thereby improves a movement degree of freedom of an X-ray tube.

Solution to Problem

A first aspect of the present invention is an X-ray inspection apparatus provided with: an X-ray tube that irradiates a subject with X-rays and can be moved in a body axial direction of the subject; X-ray tube position detecting means adapted to detect a position of the X-ray tube; an X-ray detector containing part that can be attached with a plurality of X-ray detectors having mutually different sizes in the body axial direction of the subject, and also can be moved in the body axial direction of the subject; X-ray detector containing part position detecting means adapted to detect a position of the X-ray detector containing part; X-ray detector size detecting means adapted to detect a size of an X-ray detector in the body axial direction of the subject, the X-ray detector being contained in the X-ray detector containing part; storage means adapted to store reference position information indicating whether a reference position in the body axial direction of the subject at a time when the X-ray detector is attached to the X-ray detector containing part is based on any of end edges of the X-ray detector containing part or a center of the X-ray detector containing part, and information on a maximum size of an X-ray detector in the axial direction of the subject, the X-ray detector being containable in the X-ray detector containing part; X-ray tube moving means adapted to move the X-ray tube to a position facing to the X-ray detector on a basis of information on the position of the X-ray tube, the position being detected by the X-ray tube position detecting means, information on the position of the X-ray detector containing part, the position being detected by the X-ray detector containing part position detecting means, information on the size of the X-ray detector in the body axial direction of the subject, the size being detected by the X-ray detector size detecting means, the X-ray detector being contained in the X-ray detector containing part, and the reference position information and the information on the maximum size that are stored in the storage means; and reference position information switching means adapted to, if the size of the X-ray detector in the body axial direction of the subject, the size being detected by the X-ray detector size detecting means, the X-ray detector being contained in the X-ray detector containing part, coincides with the maximum size of the X-ray detector containable in the X-ray detector containing part, enables switching of the reference position information stored in the storage means, wherein when the reference position information is switched by the reference position information switching means, the X-ray tube moving means moves the X-ray tube to a position facing to the X-ray detector in the body axial direction of the subject on a basis of a reference position resulting from the switching.

A second aspect of the present invention is configured such that, in the first aspect of the present invention, the reference position information switching means switches the reference position information to a preset reference position on a basis of a signal from an operation part operated by an operator.

A third aspect of the present invention is configured such that, in the second aspect of the present invention, the X-ray detector containing part is moved in a vertical direction in a location facing to the subject in an upright position state; and on the basis of the signal from the operation part operated by the operator, the reference position information switching means switches the reference position stored in the storage means to any of a reference position based on the center of the X-ray detector containing part, a reference position based on an upper end edge of the X-ray detector containing part, and a reference position based on a lower end edge of the X-ray detector containing part.

A fourth aspect of the present invention is configured such that, in the first aspect of the present invention, the reference position information switching means switches the reference position information to a reference position meeting a preset photographing condition.

A fifth aspect of the present invention is configured such that, in the fourth aspect of the present invention, the X-ray detector containing part is moved in a vertical direction in a location facing to the subject in an upright position state; and the reference position information switching means switches the reference position stored in the storage means to, when inspecting a chest part of the subject, a reference position based on an upper end edge of the X-ray detector containing part, and when inspecting a leg part of the subject, a reference position based on a lower end edge of the X-ray detector containing part.

A sixth aspect of the present invention is configured such that, in the first aspect of the present invention, if the size of the X-ray detector in the body axial direction of the subject, the size being detected by the X-ray detector size detecting means, the X-ray detector being contained in the X-ray detector containing part, coincides with the maximum size of the X-ray detector containable in the X-ray detector containing part, the reference position information is automatically switched to a preset reference position.

A seventh aspect of the present invention is configured such that, in the X-ray inspection apparatus according to any of the first to sixth aspects, on a basis of reference position information resulting from the switching by the reference position information switching means, the X-ray detector containing part is moved in the body axial direction of the subject.

Advantageous Effects of Invention

According to the first aspect of the present invention, by changing the reference position so as to correspond to X-ray inspection, a movement degree of freedom of the X-ray tube can be improved. For this reason, a reference position other than a reference position specific to an apparatus can be used to perform the X-ray inspection.

According to the second aspect of the present invention, the operator operates the operation part, and thereby the reference position information can be switched to the preset reference position.

According to the third aspect of the present invention, in the X-ray inspection apparatus provided with the X-ray detector containing part that is moved in the vertical direction in the location facing to the subject in the upright position state, such as an upright position stand type, the reference position can be switched between center reference based on the center of the X-ray detector containing part and upper reference based on the upper end edge of the X-ray detector containing part.

According to the fourth aspect of the present invention, by switching the reference position information to the reference position meeting the preset photographing condition, the X-ray tube can be moved to a position optimum for the photographing condition.

According to the fifth aspect of the present invention, in the X-ray inspection apparatus provided with the X-ray detector containing part that is moved in the vertical direction in the location facing to the subject in the upright position state, such as an upright position stand type, the X-ray tube can be moved to an optimum position when the chest part of the subject is inspected, or when the leg part of the subject is inspected.

According to the sixth aspect of the present invention, without the need for an operation by an operator, the X-ray tube can be automatically moved to a position optimum for a photographing condition.

According to the seventh aspect of the present invention, by moving the X-ray detector containing part in the body axial direction of the subject on the basis of the reference position information resulting from the switching by the reference position information switching means, the X-ray detector can be arranged in an optimum location so as to correspond to the movement of the X-ray tube.

DESCRIPTION OF EMBODIMENTS

Figure 1:
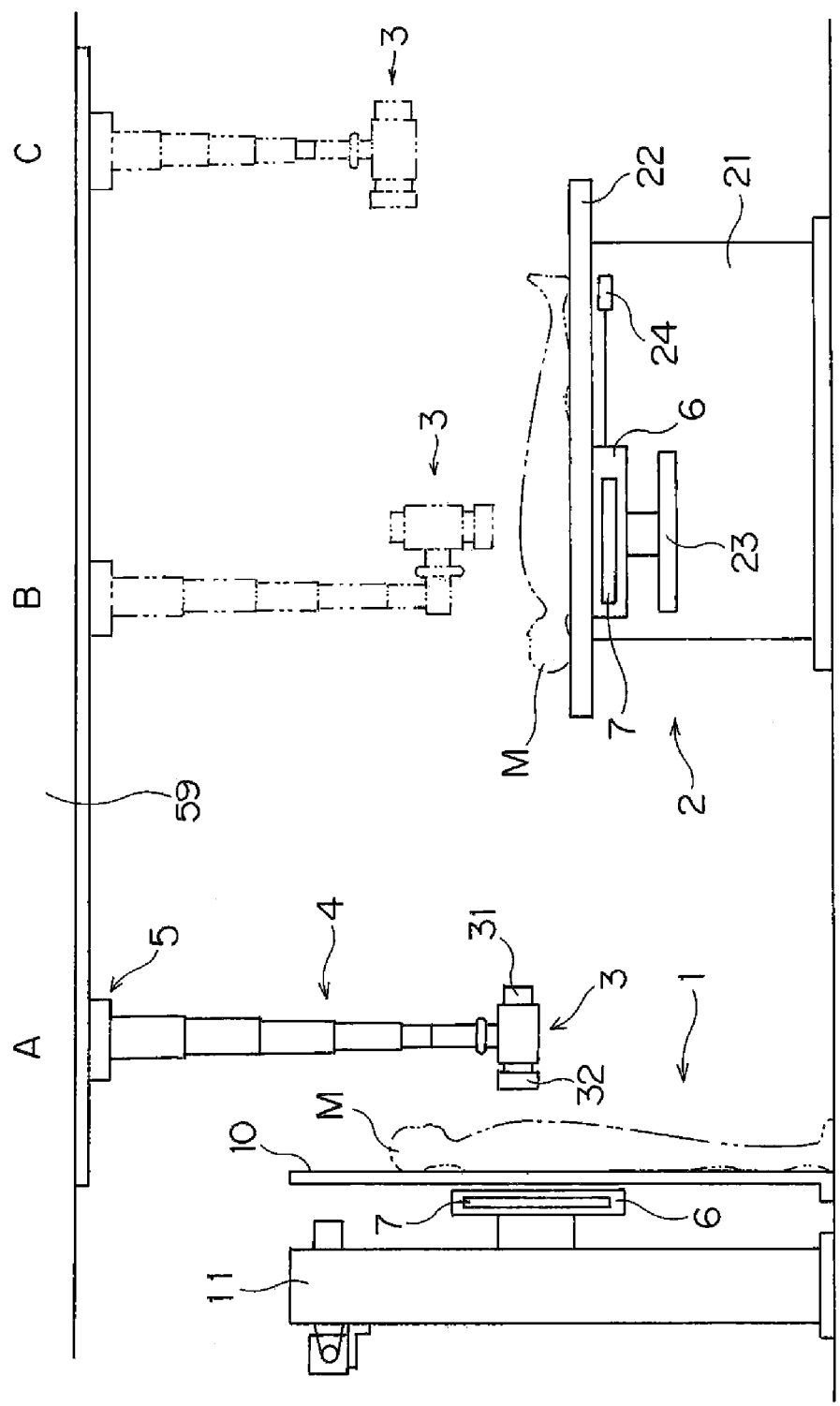
FIG. 1 is an explanatory diagram illustrating a situation of using an X-ray inspection apparatus according to the present invention to perform X-ray photography.

Embodiments of the present invention will hereinafter be described on the basis of the drawings. FIG. 1 is an explanatory diagram illustrating a situation of using an X-ray inspection apparatus according to the present invention to perform X-ray photography.

The X-ray inspection apparatus is, as illustrated in FIG. 1, provided with: an upright position stand 1 for photographing a subject M, which is a test object, in an upright posture; a supine position table 2 for photographing the subject M with laying down the subject M; an X-ray irradiation part 3 that is provided with an X-ray tube 31 and a collimator 32; a suspending and holding part 4 that, from a ceiling surface 59, suspends and holds the X-ray irradiation part 3 in a state of being able to move up and down the X-ray irradiation part 3; and a horizontal movement part 5 that horizontally moves the X-ray irradiation part 3 along the ceiling surface 59. The X-ray irradiation part 3 is configured to be able to be moved by the suspending and holding part 4 and horizontal movement part 5 to a position A indicated by a solid line, and positions B and C respectively indicated by chained lines in FIG. 1. The position A is a position where the upright position stand 1 is used to perform X-ray inspection. Also, the position B is a position where the supine position table 2 is used to perform X-ray inspection. Further, the position C is a retreated position.

The supine table 2 is provided with: a base 21; a table 22 for placing the subject M thereon; an X-ray detector containing part 6 that contains a flat panel detector 7 serving as an X-ray detector; a moving mechanism 23 that moves the X-ray detector containing part 6 in a body axial direction of the subject M on the table 22; and a potentiometer 24 for detecting a position of the X-ray detector containing part 6.

Figure 2:
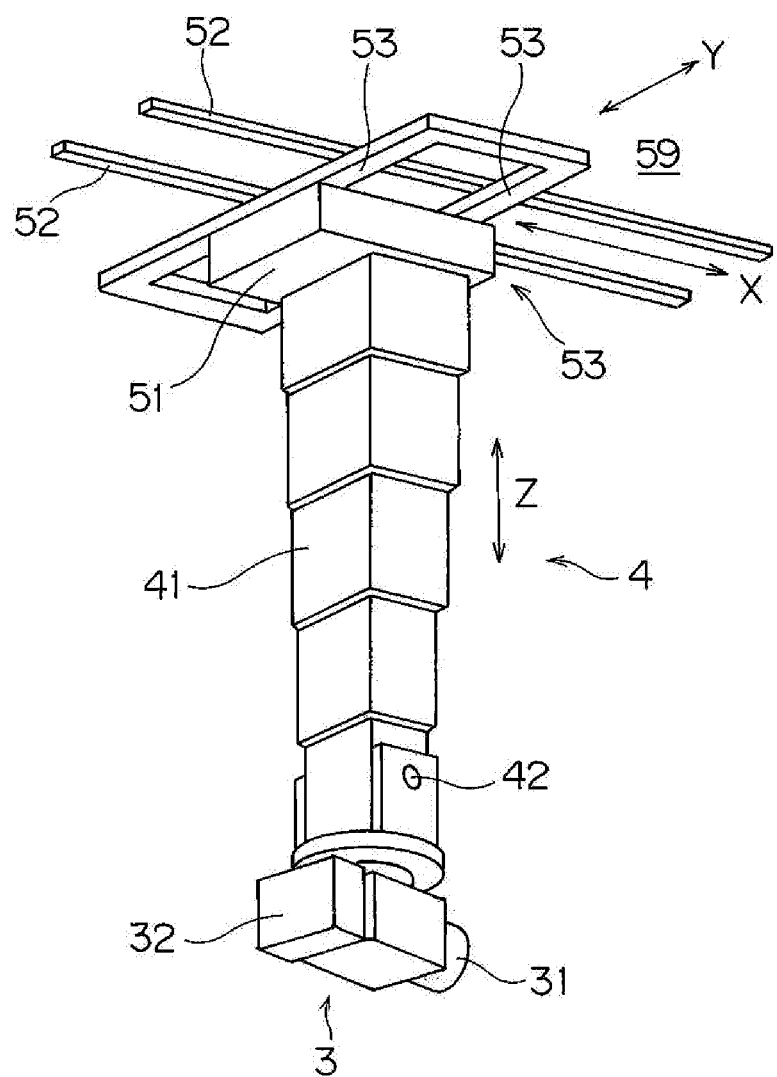
FIG. 2 is a perspective view illustrating an X-ray irradiation part 3 together with a suspending and holding part 4 and a horizontal movement part 5.

FIG. 2 is a perspective view illustrating the X-ray irradiation part 3 together with the suspending and holding part 4 and the horizontal movement part 5.

The horizontal movement part 5 is provided with: a support part 51 that is connected to the suspending and holding part 4; a pair of fixed rails 52 that is constructed on the ceiling surface 59; and a pair of movable rails 53 that is connected to the fixed rails 52 so as to be movable along the fixed rails 52. The suspending and holding part 4 is connected to the movable rails 53 through the support part 51, and the support part 51 moves integrally with the movable rails 53 in a moving direction (X direction) along the fixed rails 52, and is also connected to the movable rails 53 so as to be movable along the movable rails 53 in a direction (Y direction) orthogonal to the moving direction.

The suspending and holding part 4 is provided with a telescopic part 41 that is connected to the support part 51. The telescopic part 41 is configured to be telescopic in a vertical direction (Z direction illustrated in FIG. 2), and a lower end part of the telescopic part 4 is swingably connected with the X-ray irradiation part 3 through a shaft 42 facing in a horizontal direction. The X-ray irradiation part 3 swings around the shaft 42 to thereby come into a state of being able to irradiate X-rays in the horizontal direction at the position A in FIG. 1, or into a state of being able to irradiate the X-rays in the vertical direction at the position B in FIG. 1.

Figure 3:
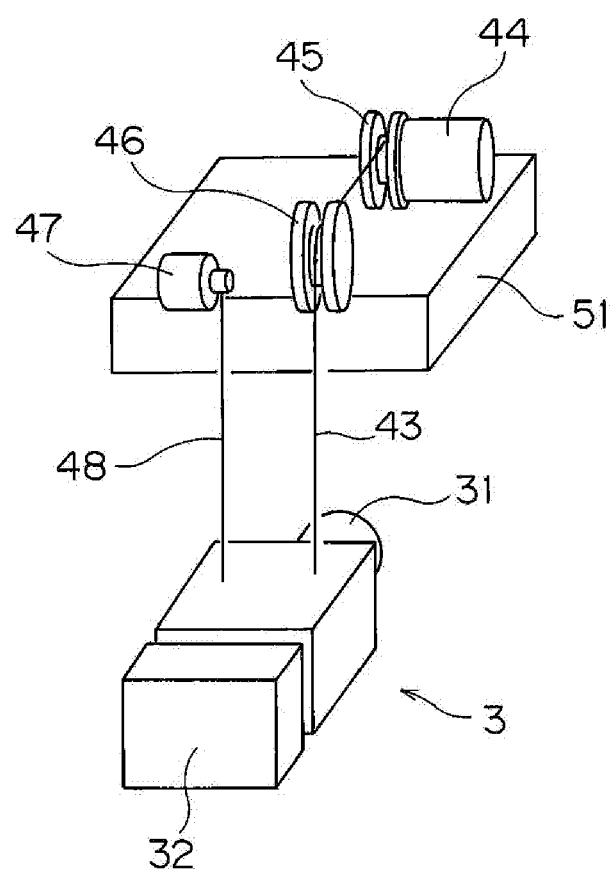
FIG. 3 is a schematic diagram schematically illustrating a hoisting mechanism of the X-ray irradiation part 3.

FIG. 3 is a schematic diagram schematically illustrating a hoisting mechanism of the X-ray irradiation part 3, which is intended to move up and down the X-ray irradiation part 3 in the Z direction.

The hoisting mechanism of the X-ray irradiation part 3 is configured to be, from the support part 51, suspended and supported by a wire 43. One end of the wire 43 is fixed to the X-ray irradiation part 3, and the other end of the wire 43 is wound around a pulley 45 that is rotated by a motor 44 fixed on the support part 51. Also, the wire 43 is guided by a pulley 46. The X-ray irradiation part 3 is moved up or down in such a way that the wire 43 is wound or wound off by the pulley 45 on the basis of driving of the motor 44. Further, the X-ray irradiation part 3 is, through a wire 48, connected to a potentiometer 47 that is fixed to the support part 51. For this reason, a height position of the X-ray irradiation part 3 is measured by the potentiometer 47, and thereby positional information on the X-ray tube 31 in the X-ray irradiation part 3 is obtained.

Figure 4:
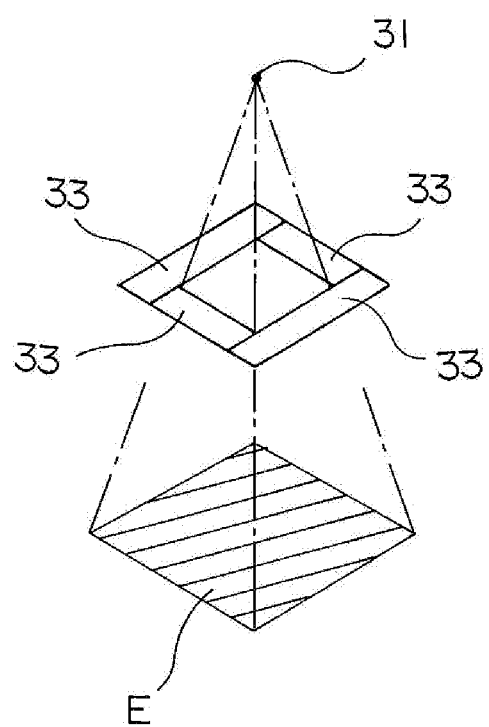
FIG. 4 is a schematic diagram of a collimator 32.

FIG. 4 is a schematic diagram of the above-described collimator 32.

The collimator 32 is provided with four collimator leaves 33. The X-rays from the X-ray tube 31 is shielded by the four collimator leaves 33, and thereby a rectangular-shaped X-ray irradiation field E is formed.

Figure 5:
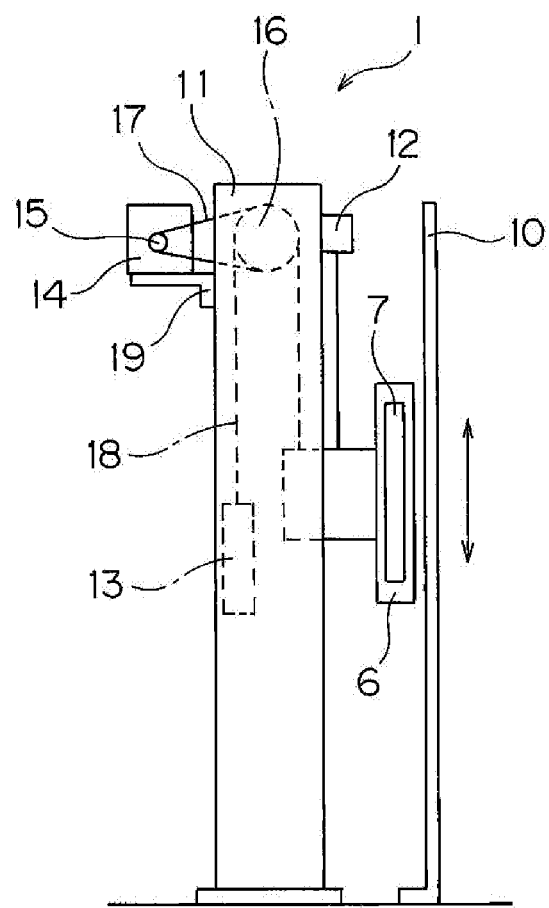
FIG. 5 is a schematic side view of an upright position stand 1.

FIG. 5 is a schematic side view of the upright position stand 1.

The upright position stand 1 is, as with the supine position table 2, provided with an X-ray detector containing part 6 that contains a flat panel detector 7 as an X-ray detector. The X-ray detector containing part 6 can be moved up and down with respect to a casing 11 by being guided by an unillustrated guide member. Also, the X-ray detector containing part 6 is connected to one end of a wire 18 that is wound around a pulley 16. The other end of the wire 18 is connected to a counter weight 13. The casing 11 is fixed with a hoisting motor 14 through a bracket 19. The pulley 16 is, through a belt 17, connected to a driving pulley 15 that is annexed to a rotary shaft of the hoisting motor 14. For this reason, the X-ray detector containing part 6 is moved up and down by driving of the hoisting motor 14. Also, a vertical position of the X-ray detector containing part 6 is detected by a potentiometer 12. On the X-ray irradiation part 3 side of the up-and-down location of the X-ray detector containing part 6, a partitioning screen 10 for preventing interference between the subject M and the X-ray detector containing part 6 is installed.

Figure 6:
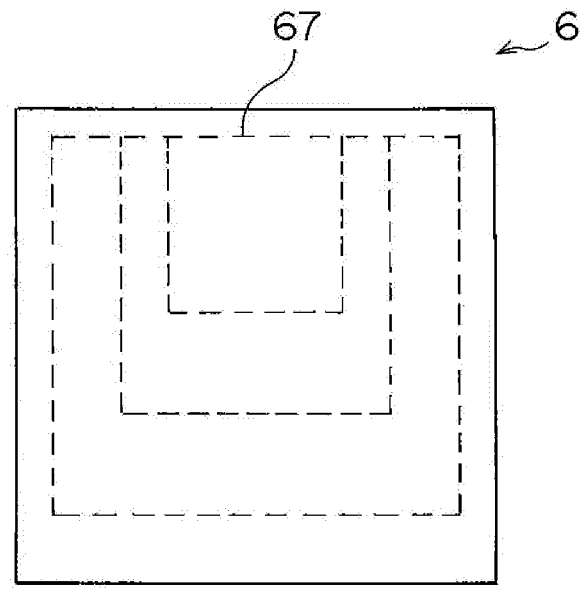
FIG. 6 is a front view of an X-ray detector containing part 6.
Figure 7:
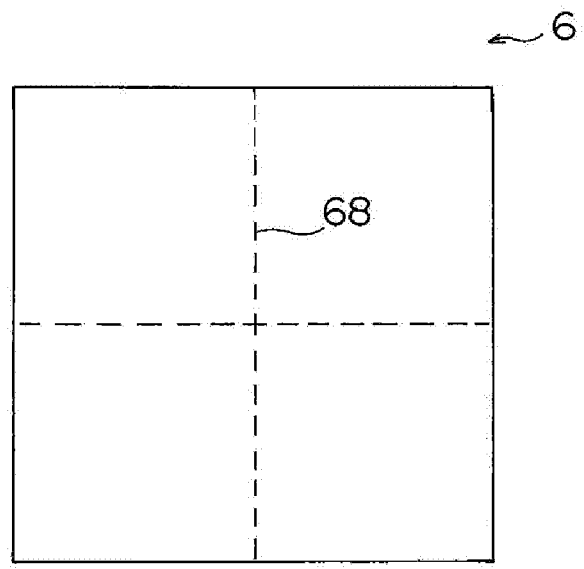
FIG. 7 is a front view of an X-ray detector containing part 6.
Figure 8:
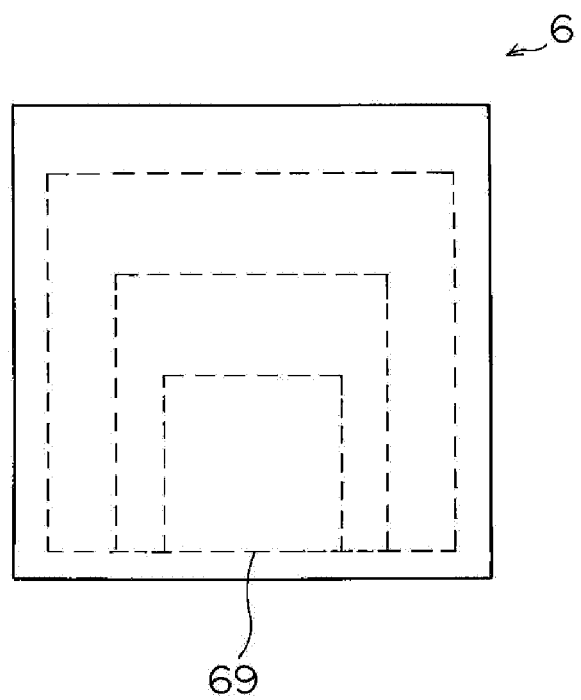
FIG. 8 is a front view of an X-ray detector containing part 6.

Next, a configuration of the X-ray detector containing part 6 that contains the flat panel detector 7 is described. FIGS. 6 to 8 are front views of X-ray detector containing parts 6, respectively.

The X-ray detector containing part 6 is configured to be attachable with not only a flat panel detector 7 having a maximum size containable therein but a plurality of X-ray detectors such as flat panel detectors 7 respectively having different sizes in the body axial direction of the subject M. Also, as the X-ray detector containing part 6, there are typically three types, i.e., an upper reference-based X-ray detector containing part 6 that uses an upper end thereof as positioning reference, a center reference-based X-ray detector containing part 6 that uses the center thereof as the positioning reference, and a lower reference-based X-ray detector containing part 6 that uses a lower end thereof as the positioning reference.

FIG. 6 illustrates the upper reference-based X-ray detector containing part 6 of which a reference position is based on the upper end of the X-ray detector containing part 6. On a surface of the X-ray detector containing part 6, marked lines 67 based on the upper end thereof are drawn. FIG. 7 illustrates the center reference-based X-ray detector containing part 6 of which a reference position is based on the center of the X-ray detector containing part 6. On a surface of the X-ray detector containing part 6, marked lines 68 based on the center thereof are drawn. FIG. 8 illustrates the lower reference-based X-ray detector containing part 6 of which a reference position is based on the lower end of the X-ray detector containing part 6. On a surface of the X-ray detector containing part 6, marked lines 69 based on the lower end thereof are drawn. The upper reference, center reference, or lower reference is the reference position that is unambiguously determined for each apparatus in terms of mechanical structure of the apparatus.

Figure 9:
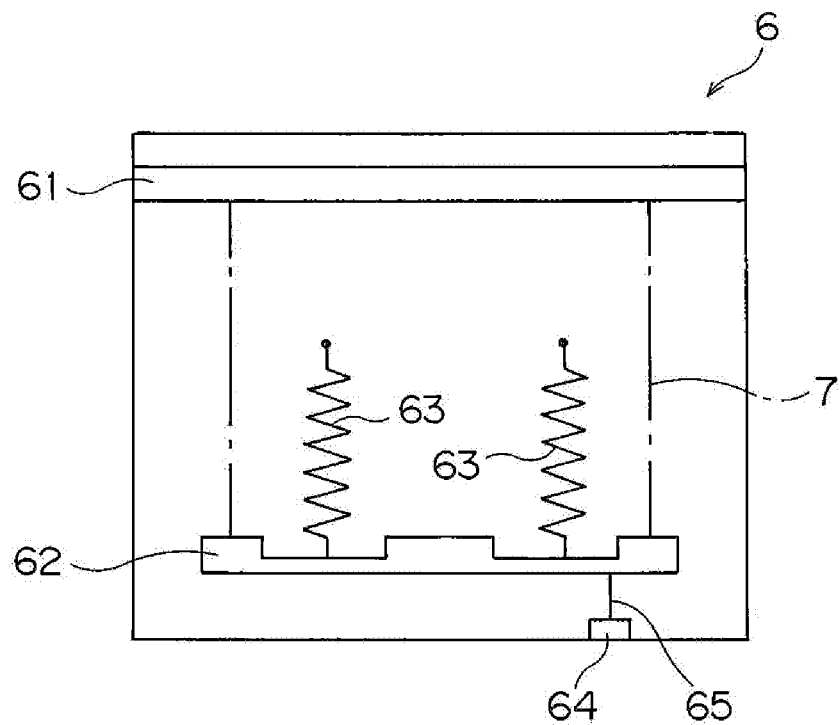
FIG. 9 is a schematic diagram illustrating internal structure of an X-ray detector containing part 6.
Figure 10:
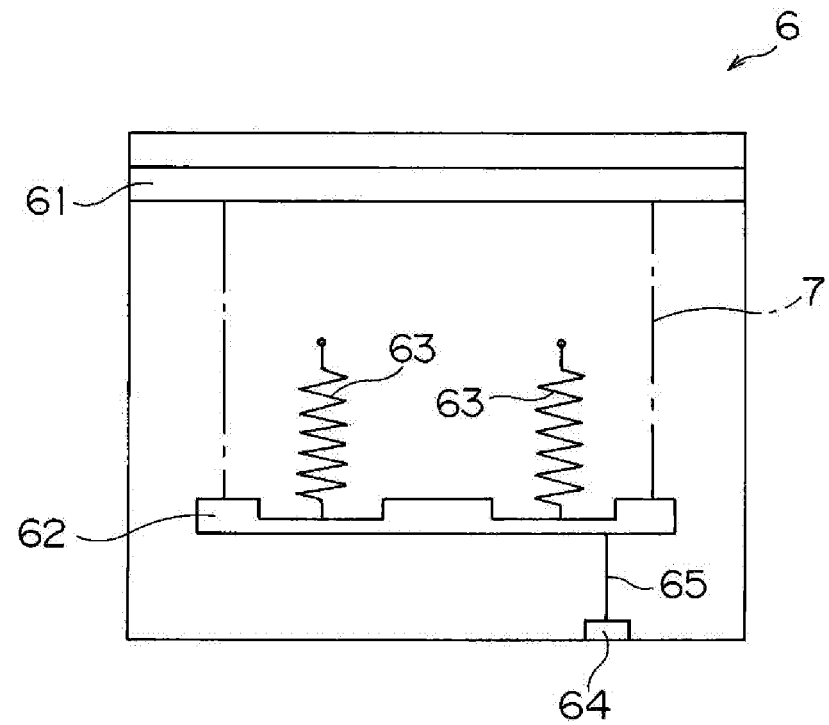
FIG. 10 is a schematic diagram illustrating the internal structure of the X-ray detector containing part 6.

FIGS. 9 and 10 are schematic diagrams illustrating internal structure of the X-ray detector containing part 6.

This X-ray detector containing part 6 is one that is used for the upright position stand 1 and positions the flat panel detector 7 indicated by virtual lines in each of the diagrams on the basis of the upper reference. The X-ray detector containing part 6 is configured to sandwich the flat panel detector 7 between a stopper piece 61 fixed to the upper end thereof and a sandwiching piece 62 biased by action of a pair of springs 63. That is, the flat panel detector 7 is positioned by an upper end thereof that is brought into abutting contact with the stopper piece 61, and fixed by a lower end thereof that is biased by the sandwiching piece 62.

As illustrated in FIG. 9, in the case where in the X-ray detector containing part 6, the flat panel detector 7 having the maximum size containable therein is contained, the sandwiching piece 62 is arranged on a lower side, whereas as illustrated in FIG. 10, in the case where in the X-ray detector containing part 6, a flat panel detector 7 having a size smaller than the maximum size containable therein is contained, the sandwiching piece 62 is arranged on an upper side. In addition, the sandwiching piece 62 is connected to a potentiometer 64 through a wire 65. The potentiometer 64 functions as X-ray detector size detecting means adapted to detect a size of the flat panel detector 7, which is contained in the X-ray detector containing part 6 as the X-ray detector, in the body axial direction of the subject M.

Figure 11:
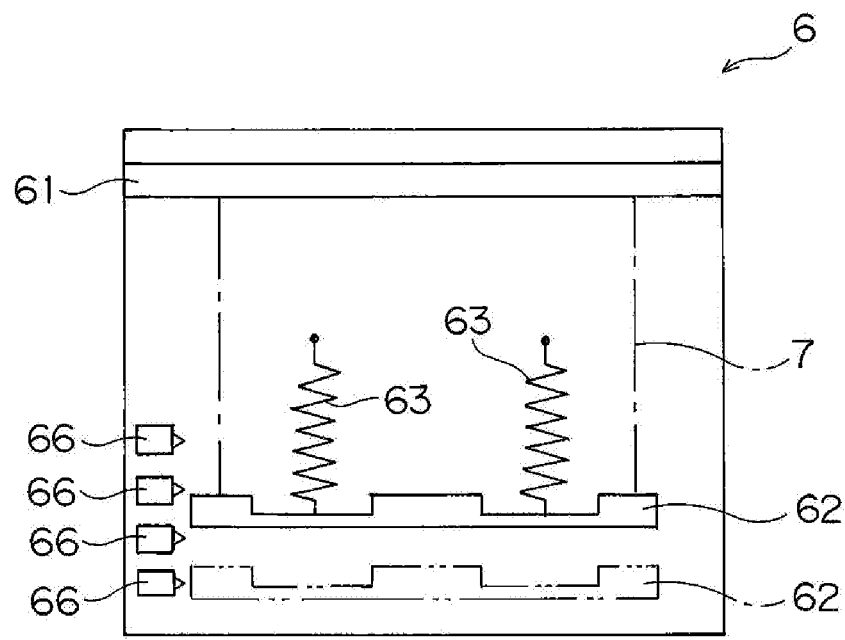
FIG. 11 is a schematic diagram illustrating internal structure of an X-ray detector containing part 6.

FIG. 11 is a schematic diagram illustrating internal structure of an X-ray detector containing part 6 according to another embodiment.

The X-ray detector containing part 6 illustrated in FIG. 11 is one that, in place of the potentiometer 64 in the X-ray detector containing part 6 illustrated in FIGS. 9 and 10, uses a plurality of micro switches 66 as the X-ray detector size detecting means.

Figure 12:
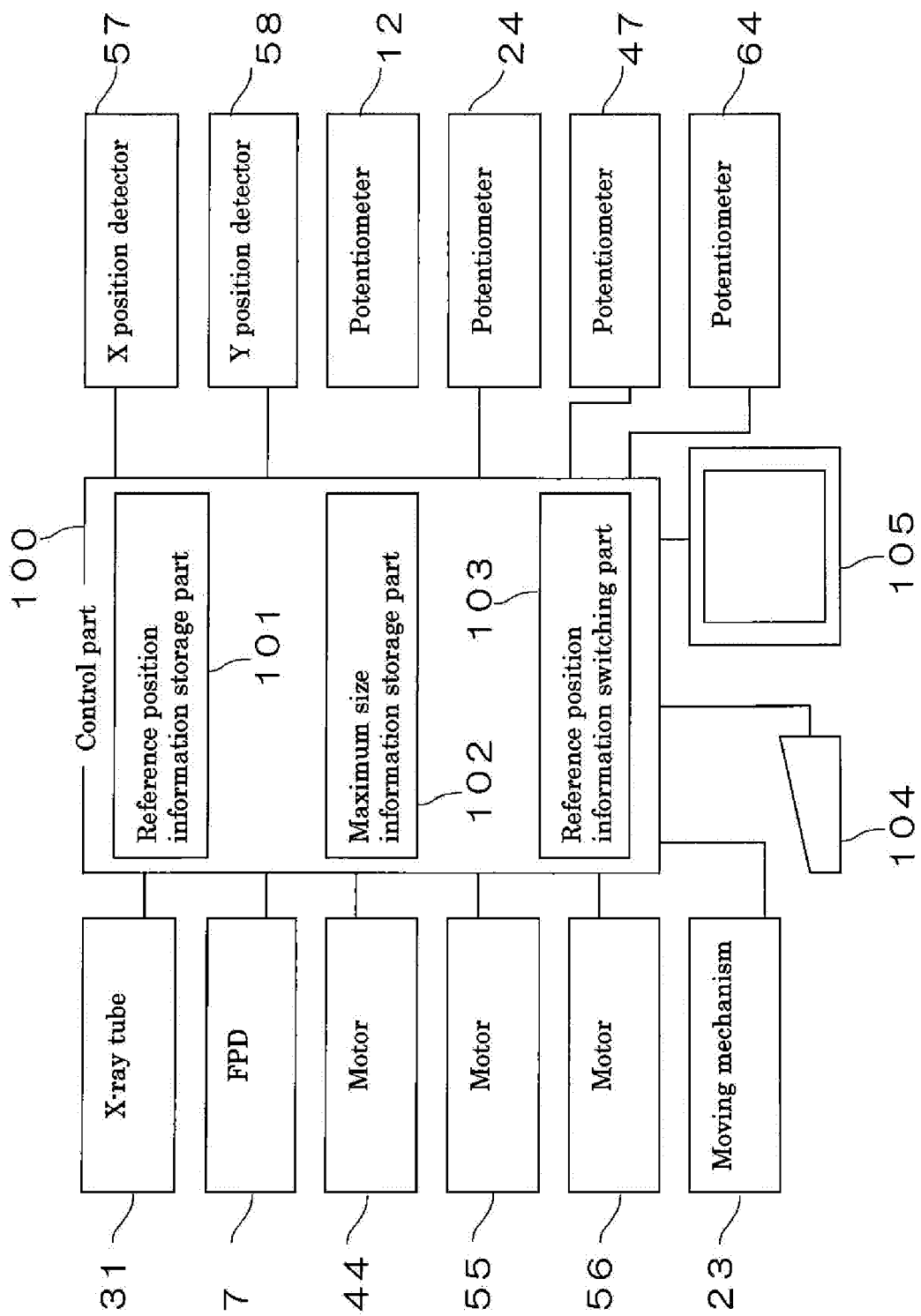
FIG. 12 is a block diagram illustrating a main electrical configuration of the X-ray inspection apparatus.

FIG. 12 is a block diagram illustrating a main electrical configuration of the above-described X-ray inspection apparatus.

The X-ray inspection apparatus is provided with a control part 100 that controls the whole of the apparatus. The control part 100 is provided with: a reference position information storage part 101 that stores reference position information indicating whether a reference position in the body axial direction of the subject M at the time of attaching the flat panel detector 7 as the X-ray detector to the X-ray detector containing part 6 is the above-described upper reference, center reference, or lower reference; and a maximum size information storage part 102 that stores information on the maximum size of the flat panel detector 7, which is containable in the X-ray detector containing part 6, in the body axial direction of the subject M. Also, the control part 100 is provided with a reference position information switching part 103 for enabling switching of the reference position information stored in the reference position information storage part 101 to another reference position under a fixed condition.

The control part 100 is connected to the above-described X-ray tube 31, flat panel detectors 7, motor 44 for moving up and down the X-ray irradiation part 3, moving mechanism 23 of the supine position table 2, potentiometer 12 for detecting a position of the X-ray detector containing part 6 in the upright position stand 1, potentiometer 24 for detecting a position of the X-ray detector containing part 6 in the supine position table 2, potentiometer 47 for detecting a height position of the X-ray irradiation part 3, and potentiometer 64 for detecting a size of the flat panel detector 7, which is contained in the X-ray detector containing part 6, in the body axial direction of the subject M.

Also, the control part 100 is connected to: a motor 55 for moving the X-ray irradiation part 3 in the moving direction (X direction) along the fixed rails 52 through the suspending and holding part 4 and horizontal movement part 5 illustrated in FIG. 1; an X position detecting part 57 for detecting a position of the X-ray irradiation part 3 in the X direction at the time of the X direction movement; a motor 56 for moving the X-ray irradiation part 3 in a moving direction (Y direction) along the movable rails 53 through the suspending and holding part 4 and horizontal movement part 5 illustrated in FIG. 1; and a Y position detecting part 58 for detecting a position of the X-ray irradiation part 3 in the Y direction at the time of the Y direction movement. Further, the control part 100 is also connected to: an operation part 104 that is provided with a numerical keypad and various types of switches; and a display part 105 that includes a CRT or a liquid crystal display panel.

Next, an X-ray photographing operation for X-ray inspection in the above-described X-ray inspection apparatus is described.

First, a first embodiment of an X-ray photographing operation in the case of using the upright position stand 1 is described. The first embodiment is adapted to, in the case of using the upright position stand 1 to photograph the subject M, switch the reference position between the center reference and the upper reference on the basis of the signal from the operation part 104 operated by the operator.

That is, in the case of performing the X-ray photography, in the control part 100, when a size of a flat panel detector 7, which is contained in the X-ray detector containing part 6, in the body axial direction of the subject M is detected, a detected value of the potentiometer 64, and the information that is stored in the maximum size information storage part 102 and on the maximum size of the flat panel detector 7, which is containable in the X-ray detector containing part 6, in the body axial direction of the subject M are compared with each other. If the size of the flat panel detector 7, which is contained in the X-ray detector containing part 6, in the body axial direction of the subject M coincides with the maximum size of the flat panel detector 7 containable in the X-ray detector containing part 6, the reference position information switching part 103 enables switching of the reference position information (in present embodiment, the upper reference) stored in the reference position information storage part 101. In the case where, in this state, the operator performs a predetermined operation on the operation part 104 by pressing a switch of the operation part 104 or performing another action, the reference position information stored in the reference position information storage part 101 is changed to a preset reference position (in present embodiment, the center reference or lower reference).

For example, in the X-ray inspection apparatus according to present embodiment, the reference position is normally set to the upper reference. For this reason, for example, in the case of inspecting a chest part of the subject M, the X-ray photography is performed on the basis of the upper reference specific to the apparatus. On the other hand, in the case of inspecting a leg part of the subject M, such as a knee, with the X-ray inspection apparatus, the X-ray detector containing part 6 is moved down together with the flat panel detector 7 by the driving of the motor 14 illustrated in FIG. 5, and along with this, the X-ray irradiation part 3 is also moved down to a position facing to the flat panel detector 7 by the driving of the motor 44 illustrated in FIG. 3.

However, the positioning reference of the flat panel detector 7 in the X-ray detector containing part 6 is the upper reference, and therefore the X-ray irradiation part 3 is moved down only to a position corresponding to the upper reference. In this case, there is a problem that, for example, if a body height of the subject M is low, and the leg part such as a knee is at a lower position, adequate photography cannot be performed unless the X-ray irradiation part 3 is further moved down manually.

However, in the X-ray inspection apparatus according to the present embodiment, if the size of the flat panel detector 7, which is contained in the X-ray detector containing part 6, in the body axial direction of the subject M coincides with the maximum size of the flat panel detector 7 containable in the X-ray detector containing part 6, the reference position information switching part 103 enables the switching of the reference position information that is stored in the reference position information storage part 101 and indicates the upper reference. Then, in the case where, in this state, the operator performs the predetermined operation on the operation part 104, the reference position information that is stored in the reference position information storage part 101 and indicates the upper reference is changed to reference position information indicating the lower reference. For this reason, the X-ray irradiation part 3 can be further moved down to a position required for the X-ray photography to perform the adequate X-ray photography.

In this regard, a more detailed description is provided. Typically, the X-ray irradiation field where the subject M is irradiated with the X-rays from the X-ray tube 31 is, in order to prevent the subject M from being exposed to excessive X-rays, limited by the above-described collimator leaves 33 in the collimator 32 and thereby made smaller than a detectable range of the flat panel detector 7. For example, in the case of performing the X-ray photography of an abdominal part, the X-ray photography is performed over a range of 14 inches×14 inches, whereas in the case of four limbs, the photography is performed over a range of 10 inches×12 inches or 8 inches×10 inches. Also, even in the case of the same site to be photographed, a size of the X-ray irradiation field is changed depending on a physical constitution of the subject M.

In the case where the reference position information that is stored in the reference position information storage part 101 and indicates the upper reference is changed to the reference position information indicating the lower reference, the information on the maximum size of the flat panel detector 7 containable in the X-ray detector containing part 6 and information on the X-ray irradiation field upon photography at the time are compared with each other to set a difference between them as an offset amount, and according to the changed reference position information, the X-ray irradiation part 3 is moved a distance corresponding to the offset amount. This enables the X-ray irradiation part 3 to be moved to a position corresponding to a size of the X-ray irradiation field based on the reference position at the time.

In addition, the movement of the X-ray irradiation part 3 at the time is carried out on the basis of: information on the position of the X-ray tube 31, which is detected by the potentiometer 47; information on the position of the X-ray detector containing part 6, which is detected by the potentiometer 12; information on the size of the flat panel detector 7, which is contained in the X-ray detector containing part 6, in the body axial direction of the subject M, which is detected by the potentiometer 64; the reference position information stored in the reference position information storage part 101; and the maximum size information stored in the maximum size information storage part 102.

As a variation of this case, if the size of the flat panel detector 7, which is contained in the X-ray detector containing part 6, in the body axial direction of the subject M coincides with the maximum size of the flat panel detector 7 containable in the X-ray detector containing part 6, the position of the X-ray detector containing part 6 may be moved upward a distance corresponding to a downward movement distance of the X-ray irradiation part 3. Even at this time, as in the above-described case of moving the X-ray irradiation part 3, the information on the maximum size of the flat panel detector 7 containable in the X-ray detector containing part 6 and the information on the X-ray irradiation field upon photography at the time are compared with each other to set a difference between them as an offset amount, and according to changed reference position information, the X-ray detector containing part 6 is moved a distance corresponding to the offset amount. In this case, the position of the X-ray detector containing part 6 is stopped at a position higher than a floor surface, and therefore the operator can easily attach or detach the flat panel detector 7 to or from the X-ray detector containing part 6.

In addition, the above-described embodiment is adapted to, if the size of the flat panel detector 7, which is contained in the X-ray detector containing part 6, in the body axial direction of the subject M coincides with the maximum size of the flat panel detector 7 containable in the X-ray detector containing part 6, enable the switching of the reference position information stored in the reference position information storage part 101, but if the size of the flat panel detector 7, which is contained in the X-ray detector containing part 6, in the body axial direction of the subject M does not coincide with the maximum size of the flat panel detector 7 containable in the X-ray detector containing part 6, disable the switching of the reference position information stored in the reference position information storage part 101. This is because if the reference position information is switched when a flat panel detector other than the flat panel detector 7 having the maximum size containable in the X-ray detector containing part 6 is contained in the X-ray detector containing part 6, a size of the flat panel detector 7 is smaller than the maximum size containable in the X-ray detector containing part 6, and therefore the upper, center, lower end of the X-ray detector containing part 6 cannot be used as reference in the case of the upper reference position, center reference position, or lower reference position. Even in the case of the same reference position information, depending on a size of a flat panel detector, a reference position with respect to the X-ray detector containing part 6 is changed, which is inconvenient to the operator.

Further, as described above, in place of switching the reference position information by the operator, the present invention may be adapted to automatically switch the reference position information. That is, the present invention may be adapted to store, as reference position forcibly switching information, a reference position to be forcibly switched thereto in the control part 100, and if the size of the flat panel detector 7 in the body axial direction of the subject M coincides with the maximum size of the flat panel detector 7 containable in the X-ray detector containing part 6, automatically switch to a predetermined reference photographing position without any operation by the operator. Specifically, in the case where the X-ray detector containing part 6 of which the mechanically unambiguously determined reference position is the center reference is used, and the upper reference is set in the control part 100 as the reference position forcibly switching information, if the size of the flat panel detector 7 in the body axial direction of the subject M coincides with the maximum size of the flat panel detector 7 containable in the X-ray detector containing part 6, the reference photographing position is immediately switched to the upper reference. In doing so, even in the case of using the center reference-based X-ray detector containing part 6, the reference photographing position can be switched to the upper reference to make basic use without any operation by the operator.

Next, a second embodiment of the X-ray photographing operation with the upright position stand 1 is described. The second embodiment is adapted to, in the case of photographing the subject M with the upright position stand 1, automatically switch the reference position information to a reference position meeting a preset photographing condition.

That is, in the case of performing the X-ray photography, in the control part 100, when the size of the flat panel detector 7, which is contained in the X-ray detector containing part 6, in the body axial direction of the subject M is detected, a detected value of the potentiometer 64, and the information that is stored in the maximum size information storage part 102 and on the maximum size of the flat panel detector 7, which is containable in the X-ray detector containing part 6, in the body axial direction of the subject M are compared with each other. If the size of the flat panel detector 7, which is contained in the X-ray detector containing part 6, in the body axial direction of the subject M coincides with the maximum size of the flat panel detector 7 containable in the X-ray detector containing part 6, as in the first embodiment, the reference position information stored in the reference position information storage part 101 can be switched. In the case where, in this state, the preset photographing condition is that for inspection of the chest part of the subject M, the X-ray photography is performed on the basis of the upper reference specific to the apparatus. On the other hand, in the case where the preset photographing condition is that for inspection of the leg part of the subject M, such as a knee, the reference position information stored in the reference position information storage part 101 is automatically changed to a preset reference position. Then, as in the case of the first embodiment, the X-ray irradiation part 3 is moved down to a position corresponding to the lower reference required for the X-ray photography, and thereby adequate X-ray photography can be performed.

Note that, in the above-described first or second embodiment, the reference position is switched between the upper reference and the lower reference. However, the present invention may be adapted to switch the reference position between the center reference and the upper or lower reference. For example, typically, in Japan, the upper reference is frequently used, whereas in Europe and America, the center reference is frequently used. For this reason, the present invention may be adapted to, depending on a situation of using the X-ray inspection apparatus, change the reference position.

Next, an embodiment of an X-ray photographing operation in the case of using the supine position table 2 is described. Even in the case of performing the X-ray photography with the supine position table 2, in the same manner as that in any of the above-described embodiments, the reference position can be changed.

In this case, as in any of the above-described embodiments, in the control part 100, when the size of the flat panel detector 7, which is contained in the X-ray detector containing part 6, in the body axial direction of the subject M is detected, a detected value of the potentiometer 64, and the information that is stored in the maximum size information storage part 102 and on the maximum size information of the flat panel detector 7, which is containable in the X-ray detector containing part 6, in the body axial direction of the subject M are compared with each other. If the size of the flat panel detector 7, which is contained in the X-ray detector containing part 6, in the body axial direction of the subject M coincides with the maximum size of the flat panel detector 7 containable in the X-ray detector containing part 6, as in the first embodiment, the reference position information stored in the reference position information storage part 101 can be switched. In the case where, in this state, the operator performs the predetermined operation on the operation part 104 by pressing a switch of the operation part 104 or performing another action, or according to the preset photographing condition, the reference position is changed. Then, the X-ray irradiation part 3 is moved in the X-direction, which is the body axial direction of the subject M on the table 22, by the driving of the motor 44 illustrated in FIG. 12. A position of the X-ray irradiation part 3 at this time is detected by the X position detector 57 illustrated in FIG. 12.

In this case, the X direction movement of the X-ray irradiation part 3 at this time is carried out on the basis of: information on the position of the X-ray tube 31, which is detected by the X position detector 57; information on the position of the X-ray detector containing part 6, which is detected by the potentiometer 24; information on the size of the flat panel detector 7, which is contained in the X-ray detector containing part 6, in the body axial direction of the subject M, which is detected by the potentiometer 64; the reference position information stored in the reference position storage part 101; and the maximum size information stored in the maximum size information storage part 102.

Even in this case, if the size of the flat panel detector 7, which is contained in the X-ray detector containing part 6, in the body axial direction of the subject M coincides with the maximum size of the flat panel detector 7 containable in the X-ray detector containing part 6, the position of the X-ray containing part 6 may be moved by the moving mechanism 23 in the X direction a distance corresponding to a movement distance of the X-ray irradiation part 3 in the X direction.

Note that, in any of the above-described embodiments, as the X-ray detector, the flat panel detector 7 is used; however, another X-ray detector such as a cassette or CR may be used, and such X-ray detectors may be used one after the other.

Reference Signs List

1 Upright position stand
2 Supine position table
3 X-ray irradiation part
4 Suspending and holding part
5 Horizontal movement part
6 X-ray detector containing part
7 Flat panel detector
10 Partitioning screen
11 Casing
12 Potentiometer
14 Hoisting motor
22 Table
23 Moving mechanism
24 Potentiometer 31 X-ray tube
32 Collimator
33 Collimator leaf
41 Telescopic part
42 Shaft
43 Wire
47 Potentiometer
48 Wire
51 Support part
52 Fixed rail
53 Movable rail
61 Stopper piece
62 Sandwiching piece
63 Spring
100 Control part
101 Reference position information storage part
102 Maximum size information storage part
103 Reference position information switching part
M Subject

The invention claimed is:

1. An X-ray inspection apparatus comprising:
an X-ray tube that irradiates a subject with X-rays and can be moved in a body axial direction of the subject;
X-ray tube position detecting means adapted to detect a position of the X-ray tube;
an X-ray detector containing part that can be attached with a plurality of X-ray detectors having mutually different sizes in the body axial direction of the subject, and also can be moved in the body axial direction of the subject;
X-ray detector containing part position detecting means adapted to detect a position of the X-ray detector containing part;
X-ray detector size detecting means adapted to detect a size of an X-ray detector in the body axial direction of the subject, the X-ray detector being contained in the X-ray detector containing part;
storage means adapted to store reference position information indicating whether a reference position in the body axial direction of the subject at a time when the X-ray detector is attached to the X-ray detector containing part is based on any of end edges of the X-ray detector containing part or a center of the X-ray detector containing part, and information on a maximum size of an X-ray detector in the axial direction of the subject, the X-ray detector being containable in the X-ray detector containing part;
X-ray tube moving means adapted to move the X-ray tube to a position facing to the X-ray detector on a basis of information on the position of the X-ray tube, the position being detected by the X-ray tube position detecting means, information on the position of the X-ray detector containing part, the position being detected by the X-ray detector containing part position detecting means, information on the size of the X-ray detector in the body axial direction of the subject, the size being detected by the X-ray detector size detecting means, the X-ray detector being contained in the X-ray detector containing part, and the reference position information and the information on the maximum size that are stored in the storage means; and
reference position information switching means adapted to, if the size of the X-ray detector in the body axial direction of the subject, the size being detected by the X-ray detector size detecting means, the X-ray detector being contained in the X-ray detector containing part, coincides with the maximum size of the X-ray detector containable in the X-ray detector containing part, enables switching of the reference position information stored in the storage means, wherein
when the reference position information is switched by the reference position information switching means, the X-ray tube moving means moves the X-ray tube to a position facing to the X-ray detector in the body axial direction of the subject on a basis of a reference position resulting from the switching.

2. The X-ray inspection apparatus according to claim 1, wherein the reference position information switching means switches the reference position information to a preset reference position on a basis of a signal from an operation part operated by an operator.

3. The X-ray inspection apparatus according to claim 2, wherein:
the X-ray detector containing part is moved in a vertical direction in a location facing to the subject in an upright position state; and
on the basis of the signal from the operation part operated by the operator, the reference position information switching means switches the reference position stored in the storage means to any of a reference position based on the center of the X-ray detector containing part, a reference position based on an upper end edge of the X-ray detector containing part, and a reference position based on a lower end edge of the X-ray detector containing part.

4. The X-ray inspection apparatus according to claim 1, wherein
the reference position information switching means switches the reference position information to a reference position meeting a preset photographing condition.

5. The X-ray inspection apparatus according to claim 4, wherein:
the X-ray detector containing part is moved in a vertical direction in a location facing to the subject in an upright position state; and
the reference position information switching means switches the reference position stored in the storage means to, when inspecting a chest part of the subject, a reference position based on an upper end edge of the X-ray detector containing part, and when inspecting a leg part of the subject, a reference position based on a lower end edge of the X-ray detector containing part.

6. The X-ray inspection apparatus according to claim 1, wherein
if the size of the X-ray detector in the body axial direction of the subject, the size being detected by the X-ray detector size detecting means, the X-ray detector being contained in the X-ray detector containing part, coincides with the maximum size of the X-ray detector containable in the X-ray detector containing part, the reference position information is automatically switched to a preset reference position.

7. The X-ray inspection apparatus according to claim 1, wherein
on a basis of reference position information resulting from the switching by the reference position information switching means, the X-ray detector containing part is moved in the body axial direction of the subject.

8. The X-ray inspection apparatus according to claim 2, wherein
on a basis of reference position information resulting from the switching by the reference position information switching means, the X-ray detector containing part is moved in the body axial direction of the subject.

9. The X-ray inspection apparatus according to claim 3, wherein
- on a basis of reference position information resulting from the switching by the reference position information switching means, the X-ray detector containing part is moved in the body axial direction of the subject.

10. The X-ray inspection apparatus according to claim 4, wherein
- on a basis of reference position information resulting from the switching by the reference position information switching means, the X-ray detector containing part is moved in the body axial direction of the subject.

11. The X-ray inspection apparatus according to claim 5, wherein
- on a basis of reference position information resulting from the switching by the reference position information switching means, the X-ray detector containing part is moved in the body axial direction of the subject.

12. The X-ray inspection apparatus according to claim 6, wherein
- on a basis of reference position information resulting from the switching by the reference position information switching means, the X-ray detector containing part is moved in the body axial direction of the subject.

* * * * *